(12) United States Patent
Zhou et al.

(10) Patent No.: US 11,331,064 B2
(45) Date of Patent: May 17, 2022

(54) METHOD AND APPARATUS FOR COMPUTED TOMOGRAPHY (CT) AND MATERIAL DECOMPOSITION WITH PILE-UP CORRECTION CALIBRATED USING REAL PULSE PILEUP EFFECT AND DETECTOR RESPONSE

(71) Applicant: CANON MEDICAL SYSTEMS CORPORATION, Otawara (JP)

(72) Inventors: Jian Zhou, Vernon Hills, IL (US); Zhou Yu, Vernon Hills, IL (US); Yan Liu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 31 days.

(21) Appl. No.: 16/915,722

(22) Filed: Jun. 29, 2020

(65) Prior Publication Data
US 2020/0323508 A1    Oct. 15, 2020

Related U.S. Application Data

(62) Division of application No. 15/951,329, filed on Apr. 12, 2018, now Pat. No. 10,869,646.

(51) Int. Cl.
*A61B 6/00* (2006.01)
*A61B 6/04* (2006.01)
*A61B 6/02* (2006.01)

(52) U.S. Cl.
CPC ............ *A61B 6/5205* (2013.01); *A61B 6/025* (2013.01); *A61B 6/0407* (2013.01);
(Continued)

(58) Field of Classification Search
CPC ....... A61B 6/025; A61B 6/032; A61B 6/0407; A61B 6/4208; A61B 6/4241;
(Continued)

(56) References Cited

U.S. PATENT DOCUMENTS 9,220,469 B2    12/2015  Jin
2016/0054454 A1  2/2016  Kato
(Continued)

OTHER PUBLICATIONS

B. J. Heismann, et al.; "Spectral Computed Tomography"; SPIE Press, 2014 (abstract only).
(Continued)

*Primary Examiner* — Irakli Kiknadze
(74) *Attorney, Agent, or Firm* — Oblon, McClelland, Maier & Neustadt, L.L.P.

(57) ABSTRACT

An apparatus and method are described using a forward model to correct pulse pileup in spectrally resolved X-ray projection data from photon-counting detectors (PCDs). To calibrate the forward model, which represents each order of pileup using a respective pileup response matrix (PRM), an optimization search determines the elements of the PRMs that optimize an objective function measuring agreement between the spectra of recorded counts affected by pulse pileup and the estimated counts generated using forward model of pulse pileup. The spectrum of the recorded counts in the projection data is corrected using the calibrated forward model, by determining an argument value that optimizes the objective function, the argument being either a corrected X-ray spectrum or the projection lengths of a material decomposition. Images for material components of the material decomposition are then reconstructed using the corrected projection data.

12 Claims, 10 Drawing Sheets

(52) U.S. Cl.
CPC ............ *A61B 6/4208* (2013.01); *A61B 6/502* (2013.01); *A61B 6/582* (2013.01)

(58) Field of Classification Search
CPC ..... A61B 6/4266; A61B 6/4275; A61B 6/482; A61B 6/502; A61B 6/5205; A61B 6/5258; A61B 6/582; A61B 6/585; A61B 6/03; A61B 6/4078; A61B 6/4085; A61B 6/481; A61B 6/5217; A61B 6/5282; A61B 6/04; A61B 6/4042; A61B 6/4233; A61B 6/52; A61B 6/06; A61B 6/4021; A61B 6/4035; A61B 6/4291; A61B 6/54; A61B 6/4014; G06T 11/005; G06T 11/006; G06T 2211/408; G06T 2207/10081; G06T 2211/424; G06T 11/003; G06T 2207/30004; G06T 7/0012; G06T 11/008; G06T 2207/20182; G06T 2211/421; G06T 2211/436; G06T 5/002; G06T 2207/20192; G06T 2210/41; G06T 2211/40; G06T 2211/416; G01N 23/046; G01N 2223/401; G01N 2223/419; G01N 23/044; G01N 23/087; G01N 2223/303; G01N 2223/3035; G01N 2223/505; G01N 23/083; G01N 23/20075; G01N 23/04; G01N 23/20; G01T 1/2985; G01T 1/36; G01T 1/16; G01T 1/1663; G01T 1/169; G01T 1/171; G01T 1/17; G01T 1/2928; G01V 5/0016; G06N 20/20; G06N 3/0445; G06N 3/0454; G06N 3/0472; G06N 3/084; G06N 7/005; G06N 23/046; G06N 23/083; G21K 1/025; G21K 1/10; H01J 35/26; H01J 35/30
USPC ......................................... 378/4, 5, 7, 19, 62
See application file for complete search history.

(56) References Cited

U.S. PATENT DOCUMENTS

2016/0202364 A1  7/2016  Wang
2018/0235562 A1  8/2018  Petsch ke

OTHER PUBLICATIONS

M. Kafaee, et al.; "Pile-up Correction by Genetic Algorithm and Artificial Neural Network"; Nuclear Instruments and Methods in Physics Research; vol. 607, issue 3; (2009); 652-658.

Zhicong Yu et al.; "Evaluation of conventional imaging performance in a research whole-body CT system with a photon-counting detector array"; Physics in Medicine & Biology; 25 pgs.; Feb. 21, 2016.

Okkyun Lee, et al.; "Estimation of Basis Line-Integrals in a Spectral Distortion-Modeled Photon Counting Detector Using a Low-Order Polynomial Approximation of X-ray Transmittance"; IEEE Transactions on Medical Imaging; vol. 36, No. 32; Feb. 2017; 14 pages.

Jochen Cammin, et al.; A cascaded model of spectral distortions due to spectral response effects and pulse pileup effects in a photon-counting x-ray detector for CT; Medical Physics; Apr. 2014; 16 pages.

No pileup
$\Pr(E|E_0)$

1-order pileup
$\Pr(E|E_0, E_1)$

2-order pileup
$\Pr(E|E_0, E_1, E_2)$

METHOD AND APPARATUS FOR COMPUTED TOMOGRAPHY (CT) AND MATERIAL DECOMPOSITION WITH PILE-UP CORRECTION CALIBRATED USING REAL PULSE PILEUP EFFECT AND DETECTOR RESPONSE

CROSS-REFERENCE TO RELATED APPLICATIONS

This application is a divisional of U.S. application Ser. No. 15/951,329, filed Apr. 12, 2018, the entire contents of which are incorporated herein by reference.

BACKGROUND

Field

Embodiments described herein relate generally to spectrally resolved projection data, and more specifically to correcting the projection data for pulse pileup arising in photon-counting detectors.

Description of the Related Art

Projection data can be used for many applications, including: computed tomography, radiography, mammography, and tomosynthesis. Projection data reveals the internal structure of an object by transmitting radiation through the object and detecting the effect of the object on the transmitted radiation by comparing transmitted radiation with the object present in the beam path versus when the object is absent. In absorption imaging the projection data represents Radon transforms of the attenuation along the rays traced by the radiation. Computed tomography (CT) uses projection data acquired for a series of projection angles to generate a sinogram from which an image of the internal structure of the object can be reconstructed. For example, a reconstruction algorithm, such as filtered back-projection or an iterative reconstruction method, can be used to approximate an inverse Radon transform to reconstruct a volumetric image from the series of projection images acquired at different projection angles.

CT imaging systems and methods are widely used for medical imaging and diagnosis. Typically an X-ray source is mounted on a gantry that revolves about a long axis of the body. An array of X-ray detector elements are mounted on the gantry, opposite the X-ray source. Cross-sectional images of the body are obtained by taking projective attenuation measurements at a series of gantry rotation angles, and processing the resultant projection data using a CT reconstruction algorithm.

Some CT scanners use energy-integrating detectors to measure CT projection data. Alternatively, photon-counting detectors (PCDs) have been developed using a semiconductor such as cadmium zinc telluride (CZT) capable of converting X-rays to photoelectrons to quickly and directly detect individual X-rays and their energies, which is advantageous for spectral CT. To obtain spectrally resolved projection data, the PCDs divide the X-ray beam into spectral bins (also called energy components) and count a number of photons in each of the bins. Many clinical applications can benefit from spectral CT technology, e.g., due to better material differentiation and improved beam hardening correction.

One advantage of spectral CT, and spectral X-ray imaging in general, is that materials having atoms with different atomic number Z also have different spectral profiles for attenuation. Thus, by measuring the attenuation at multiple X-ray energies, materials can be distinguished based on the spectral absorption profile of the constituent atoms (i.e., the effective Z of the material). Distinguishing materials in this manner enables a mapping from the spectral domain to the material domain, which is referred to as material decomposition.

Material decomposition of spectral CT data is possible because the attenuation of X-rays in biological materials is dominated by two physical processes—photoelectric and Compton scattering. Thus, the attenuation coefficient as a function of energy can be approximated by the decomposition $$\mu(E,x,y) = \mu_{PE}(E,x,y) + \mu_C(E,x,y),$$

wherein $\mu_{PE}(E,x,y)$ is the photoelectric attenuation and $\mu_C(E,x,y)$ is the Compton attenuation. This decomposition of the attenuation coefficient can be rearranged instead into a decomposition into two material components, with material 1 being a high-Z material such as bone and material 2 being a low-Z material such as water. Accordingly, the attenuation decomposition can be expressed as $$\mu(E,x,y) \approx \mu_1(E)c_1(x,y) + \mu_2(E)c_2(x,y),$$

wherein $c_{1,2}(x,y)$ is a spatial function describing the concentrations of material 1 and material 2 located at position (x, y). The order of image reconstruction and material decomposition can be interchanged. When material decomposition is performed before image reconstruction, the spectral resolved attenuation at the pixels is resolved into projection lengths for the materials, such that the total attenuation at a photon-counting detector (PCD) due to the $i^{th}$ material components is the product of the projection length, $L_i$, and the attenuation coefficient of the $i^{th}$ material component, $\mu_i$, at a predefined density.

While semiconductor-based PCDs provide unique advantages for spectral CT, they also create unique challenges. For example, without correcting for nonlinearities and spectral shifts in the detector response, images reconstructed from semiconductor-based PCDs can have poorer image quality. The detector response corrections can include corrections for pileup, ballistic deficit effects, polar effects, characteristic X-ray escape, and space-charge effects. The combination of detector response correction and material decomposition creates a complex problem. Accordingly, computationally efficient methods are desired to correct for the spectral and nonlinear detector response of PCDs to ensure high-quality reconstructed images.

BRIEF DESCRIPTION OF THE DRAWINGS

A more complete understanding of this disclosure is provided by reference to the following detailed description when considered in connection with the accompanying drawings, wherein.

DETAILED DESCRIPTION

Photon-counting-detector based CT system (PCCT) have many advantages, including: spectrally resolving X-ray radiation, high-spatial resolution, and low electronic noise. At high X-ray flux rates, however, photon-counting detectors can suffer from pile up. That is, due to the count rate limitation of existing ASIC and semiconductor-detector technology, the measured count can deviate from the true count when the incident flux is sufficiently high that multiple X-ray photons are frequently incident on respective detector elements within the detection time window.

Figure 1A:
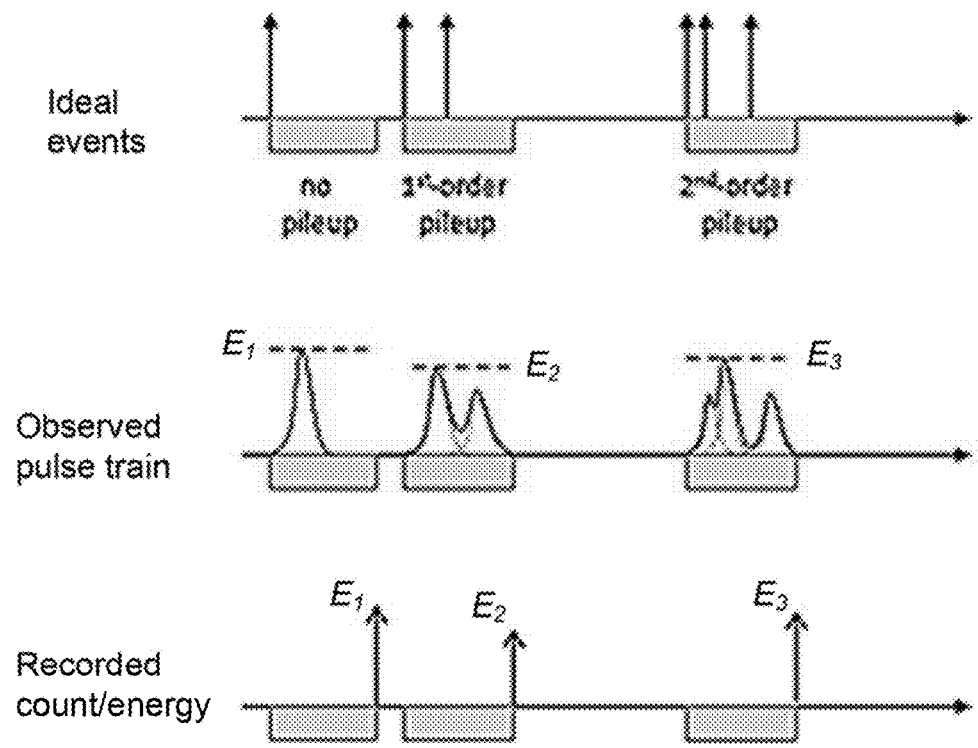
FIG. 1A shows examples of pulse trains illustrating no pileup, first-order pileup, and second-order pileup, and the signals generated for these pulse trains by an ideal detector (ideal events) and a non-ideal detector (observed pulse train), also shown are the recorded counts and energies for the non-ideal detector at the end of the respective detection windows, according to one implementation.
Figure 1B:
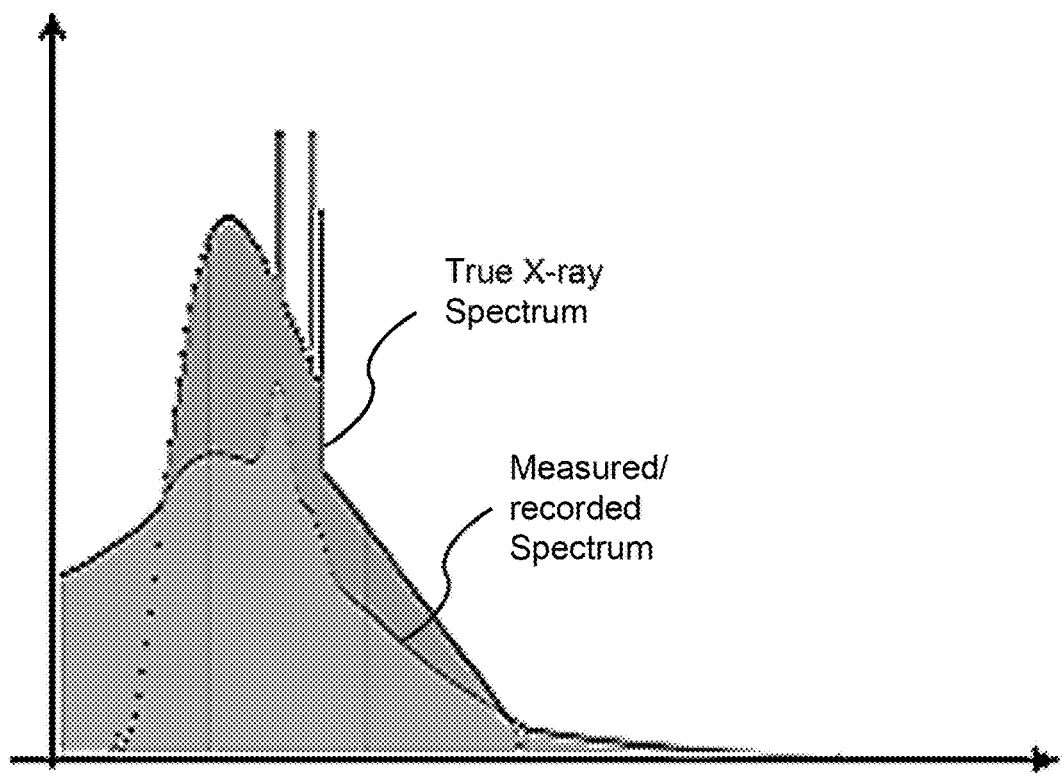
FIG. 1B shows a plot of an example of X-ray spectra for a true X-ray spectrum and a measured/recorded X-ray spectrum, illustrating a distortion due to pileup in non-ideal photon counting detectors, according to one implementation.

The pileup effect is illustrated in FIGS. 1A and 1B, which show that in first-order and higher-order pile up the recorded/measured spectrum can become shifted relative to the actual spectrum of X-rays incident on the detector elements as a result of overlap and interactions between X-ray pulses/signals within given detector element during a detection time window. For example, in an ideal nonparalyzable (NP) detector ("ideal events" in FIG. 1A), the effects at high count rates due to multiple photons arriving during the detection window manifests as the multiple photons being counted as one X-ray photon having the highest energy detected during the detection window. Thus, even for this "ideal" case, the output count no longer accurately reflects the true counts, and the detected spectrum is distorted relative to the true spectrum. This effect is known as pulse pile up.

Moreover, for non-ideal detectors, physical effects due, e.g., to charge interactions between photo-electrons, depletion, saturation effects, etc. can cause further distortions of the measured spectrum relative to the true spectrum, as illustrated in the "observed pulse train" and "recorded count/energy" examples shown in FIG. 1A. Thus, the practical effect of pulse pile up is to shift of the recorded/measured energy spectrum relative to the true energy spectrum, as shown in FIG. 1B.

If left uncorrected, the detector response determines the distribution of actually energy deposited in photon counting detector, and an inaccurate response model will induce errors to the photon energy distributions, causing inaccurate decomposition results. Several strategies can counteract or otherwise minimize the effects of pileup. For example, making the area of detector elements smaller pushes the flux threshold higher before pileup becomes an issue, but the pileup effect still must be corrected for when this higher flux threshold is exceeded. When pixel size decreases and the flux rate per area is held constant, the count rate per pixel decreases proportionally to the decrease in detector area. Thus, small pixel design mitigates the pileup problem to a degree, but is not a complete solution. Moreover, decreasing the pixel size present other challenges, such as increasing charge sharing effects, which, like pile up, also causes spectral distortion and degrades the image quality and performance of the imaging system.

Additionally, an analytical model can be used to estimate and then correct for the pile-up effect. However, analytical models are limited by that fact that they are based on the analytical pulse shape an ideal NP detector, which is illustrated in FIG. 1A, and is not representative of the real detector response, leading to the model mismatch that could affect the accuracy of subsequent processing steps such as material decomposition and image reconstruction. Further, using analytical models for spectrum correction and then material decomposition would require the evaluation of a complete pileup response function, which is resource intensive both in terms of storage and computation. For example, precomputing and storing an analytical model would demand a lot of storage space and hence would not be practical, in particular, when the full pileup response function varies from element-to-element of the detector array. Alternatively, calculating the pileup response function on-the-fly is also not currently practical because of the length of time these computations would require.

Using heuristic models such as a neural network to correct for the detector response also have their drawbacks. For example, these methods require a large set of training data to estimate the model parameters. But even with a large set of training data, the training does not guarantee a global minimizer because the objective function used for training is nonconvex, posing an obstacle to maintaining steadibility and robustness when correcting for pileup using a neural network. Also, the use the neural network method for the pileup correction with realistic detector is an under-developed field that remains poorly understood.

To address the above-discussed challenges presented by the pileup effect in non-ideal detectors, the methods described herein apply a parametric pile-up model accounting for the real detector response, as described below. In certain implementations, the methods described herein use a low-dimensional parametric pile-up forward model based on real detector response for PCCT. Further, the methods described herein can include a material decomposition method that is integrated with the forward model for pileup correction. For example, the parametric pile-up model can be represented using a sequence of low dimensional pile-up matrices corresponding to respective orders of pileup, and the dimensionality of the pile-up matrix grows with the order of pileup, as described below. Further, the model parameters of the pile-up model can be directly estimated from a set of calibration scans acquired using the real detector to be calibrated. Advantageously, this estimation of the model parameters is convex, and, hence, guarantees a global minimizer that allows for optimal performance. In certain implementations, the methods described herein also incorporate material decomposition together with the estimated pile-up model to recover from the measured projection data, which has a distorted spectrum, corrected projection data representing the true un-distorted spectrum of the X-rays incident on and detected at the detector. Alternatively, when the pileup correction is integrated with material decomposition, as discussed below, the methods described herein can directly generate path lengths for the basis-materials of the material decomposition.

Figure 2:
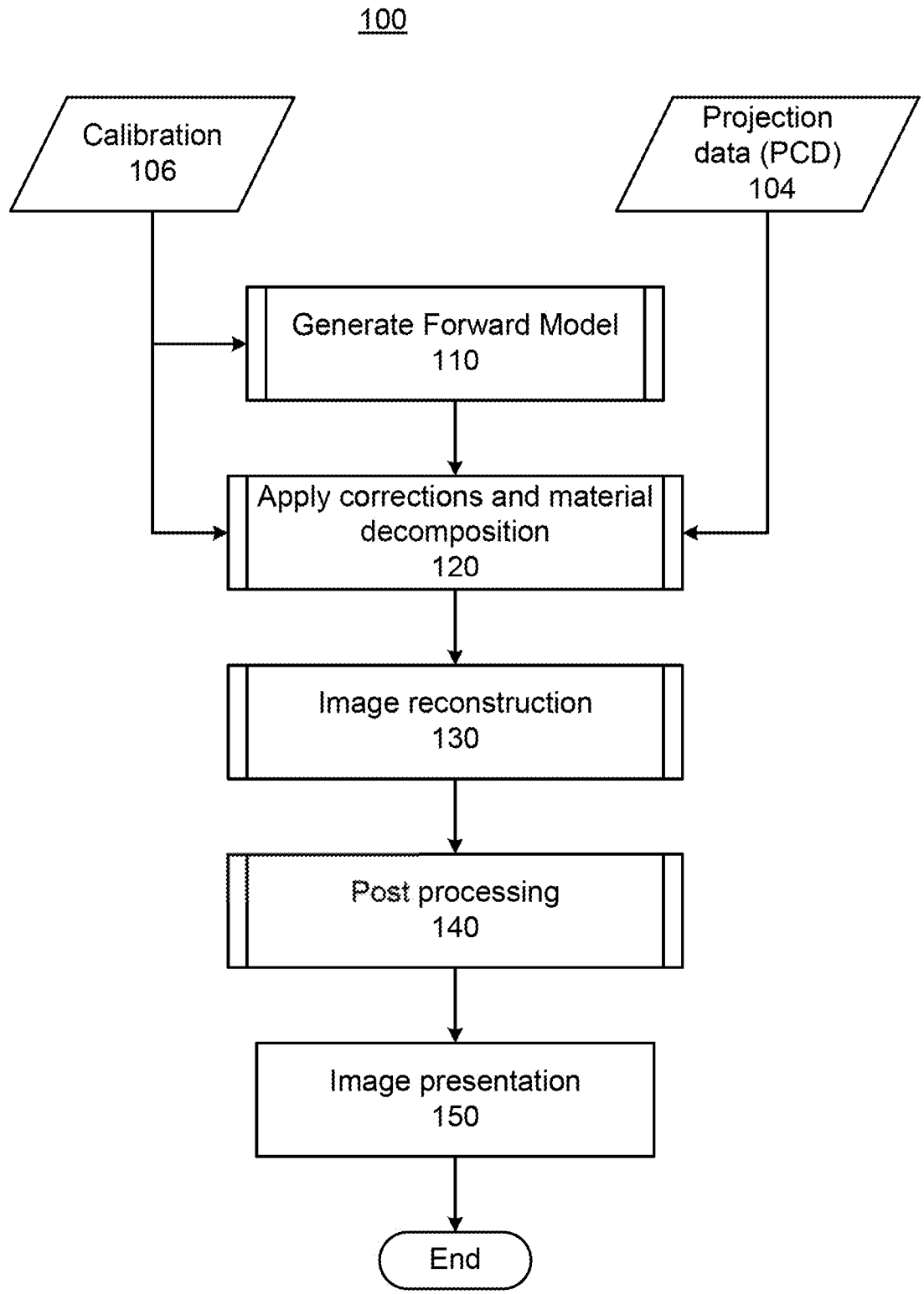
FIG. 2 shows a flow diagram of a method to correct projection data using a forward model of pileup, and then reconstruct a computed tomography (CT) image using the corrected projection data, according to one implementation.

Referring now to the drawings, wherein like reference numerals designate identical or corresponding parts throughout the several views, the methods described herein can be better appreciated by considering the non-limiting flow diagram of method 100, shown in FIG. 2. FIG. 2 shows a flow diagram of method 100, which is an overall workflow of a PCCT pileup correction, material decomposition, and image reconstruction method. The above discussed improvements and advantages of the methods described herein are variously included in implementations of processes 110 and 120, which are directed to generating a forward model representing the real pileup effect and detector response measured in the calibration data 106 to correct for pileup; and (ii) performing a material decomposition. That is, in spectral CT using photon-counting detectors (PCDs), an image reconstruction process 130 is preceded by preprocessing steps including correcting for the detector response and material decomposition.

FIG. 1 shows a flow diagram of method 100 for reconstructing an image of an object OBJ based on a series of projection measurements of the object OBJ performed at different projection directions (i.e., computed tomography (CT) using projective measurements). The data processing is performed using two inputs—calibration values 106 and projection data 104. The projection data have multiple spectral components, making it compatible with material decomposition based on the different spectral absorption characteristics of high-Z and low-Z materials. In addition to being applicable to CT applications as illustrated by the non-limiting example in FIG. 2, processes 110 and 120 are also applicable to non-CT applications involving projective measurements, including radiography, mammography, and tomosynthesis, which are within the scope of the apparatuses and methods described herein and do not depart from the spirit of this disclosure, as would be appreciated by a person of ordinary skill in the art.

Process 110 of the image reconstruction method 100 corrects the projection data for the real detector response, including pileup. This can include using various calibrations 106 to precompute a feed forward model.

Next, the method 100 proceeds to process 120, in which the spectrally resolved projection data is corrected to account for pulse pileup using the feed forward model, and various other calibrations can be applied to correct the projection data (e.g., denoising, background subtraction, corrections for nonlinear-detector response, etc.). The corrections can be applied prior to, after, or in conjunction with the decomposition of the spectral components into material components, while still in the projection domain (i.e., before image reconstruction).

Although images of the object OBJ can be reconstructed from the spectral components of the projection data and then material decomposition is performed in the image domain on these spectral-component images without departing from the spirit of the disclosure, this alternative order of the processing steps will not be described in the non-limiting example illustrated in FIG. 2.

After process 120, the method 100 proceeds to process 130 wherein multiple images are reconstructed using an image reconstruction process (e.g., an inverse Radon transformation). The image reconstruction can be performed using a back-projection method, a filtered back-projection, a Fourier-transform-based image reconstruction method, an iterative image reconstruction method (e.g., algebraic reconstruction technique or the like), a matrix-inversion image reconstruction method, or a statistical image reconstruction method. For non-CT applications (e.g., radiography, mammography, and tomosynthesis), process 130 is omitted, and the non-CT application can proceed directly from process 120 to either process 140 or process ISO.

After process 130, the method 100 proceeds to process 140 wherein post-processing steps are performed on the data, including: volume rendering, smoothing, densoing, filtering, and various methods for combining the material images to convey physical concept (e.g., maps of the attenuation, density, or effective Z density).

Finally, in step 150 of method 100 the image is presented to a user. The image presentation can be performed by displaying the image on a digital screen (e.g., LCD monitor), by printing the image on a suitable medium (e.g., paper or an X-ray film), or by storing the image on a computer-readable medium.

The discussion herein is focused primarily on process 110 and process 120. As discussed above, these processes are applicable to both CT and non-CT applications, including: radiography, mammography, and tomosynthesis, which are within the applications of the methods described herein, as would be understood by a person of ordinary skill in the art.

In summary, according to a nonlimiting implementation, method 100 includes, at process 110, generating a lower dimension pulse pileup model/parameters in forward model, which is precomputed from calibration data 106 with real detector response and the stored in a non-transitory computer readable medium of a CT apparatus. Further, method 100 includes, at process 120, applying material decomposition, either after or together with the application of the precomputed pileup model, to projection data 104 from photon-counting detectors (PCDs) to compute the path length of different material from real PCCT measurements. At process 130, method 100 includes reconstructing material images from the material-component path lengths/sinograms generated at process 120. The reconstruction method used in process 130 can be any known method, including analytical reconstruction methods and iteration reconstruction methods. At process 140, method 100 includes post-processing such as artifact reduction techniques that are applied to further improve image quality.

The discussion below focuses primarily on process 110 and process 120. As discussed above, these processes are applicable to both CT and non-CT applications, including: radiography, mammography, and tomosynthesis, which are within the spirit of the disclosure, as would be understood by a person of ordinary skill in the art.

Returning to process 110, the projection data correction can be represented by the recorded/measured energy $S_{out}(E)$ derived from the energy spectrum of X-rays incident on the detector $S_{in}(E)$, wherein an implementation of the detector response function is given by $$S_{out}(E) = ne^{-n\tau} \int dE_0 R_0(E, E_0) S_{in}(E_0) + n^2 e^{-n\tau} \iint dE_0 dE_1 R_1(E, E_0, E_1) S_{in}(E_0) S_{in}(E_1) | \text{higher order}$$

wherein $R_0$ is the linear response function, $R_1$ is the quadratic response function representing first-order pileup, and $\tau$ is the dead time of the detector. Each of $R_0$, $R_1$, and $\tau$ can depend on the detector element and the incident angle of the X-ray radiation. Additionally, the recorded/measured energy $S_{out}(E)$ also depends on higher-order terms, including second-order pileup, etc. The incident spectrum is given by $$S_{in}(E_i) = S_{air}(E) \exp[-\mu_1(E)L_1 - \mu_2(E)L_2],$$

wherein $\mu_1$ and $\mu_2$ are the attenuation coefficients of the basis materials for the material decomposition, $L_1$ and $L_2$ are the projection lengths and $S_{air}$ is the X-ray radiation in the absence of attenuation due to an imaged object OBJ (i.e., when $\mu_1 = \mu_2 = 0$).

The number of counts in a given energy bin is calculated by the expression $$N_k = \Delta T \int dE \, w_k(E) S_{in}(E),$$

wherein $\Delta T$ is the integration time and $w_k(E)$ is the spectral function of the $k^{th}$ energy bin of the photon counting detectors. For example, the spectral function could be a square function, which is defined as $$w_k(E) = \begin{cases} 1 & W_k < E < W_{k+1} \\ 0 & \text{otherwise} \end{cases}.$$

The discretization of the detected energy spectrum into energy bins enables the simplification of the feed-forward model. Accordingly, the general forward model of PCCT detector with the pileup effect can be described as:

$$S_{out}(E) = \lambda_M \cdot \Delta T \cdot \sum_{m=0}^{\infty} P(E|m, S_{in}) Pr(m),$$

wherein $S_{out}(E)$ is the output spectrum, $\lambda_M$ is the measured count rate, $\Delta T$ is the scan time, $P(E|m, S_{in})$ is the mth-order pileup spectrum, $Pr(m)$ is the probability of having the m order pileup (i.e., it is determined from Poisson statistics). Further, the mth-order pileup spectrum can be expressed by:

$$P(E|m, S_{in}) = \int \ldots \int Pr(E|E_0, \ldots, E_m) S_{in}(E_0) \ldots S_{in}(E_m) dE_0 \ldots dE_m$$

wherein $S_{in}(E_i)$ represents the input energy spectrum energy, $Pr(E|E_0, \ldots, E_m)$ is a conditional probability density function that the recorded/measured energy will be E given that the energies the m+1 X-rays incident on the detector element in the time window $\Delta T$ are $\{E_0, E_1, \ldots, E_m\}$. Since $Pr(E|E_0, \ldots, E_m)$ is determined by detector response for pulse pileup, and is called the pileup response function (PRF). Using the methods described below to estimate the PRF, pileup correction can be performed to account for real physical effects and detector properties. The methods described below are advantageous because they overcome the significant obstacles resulting from the facts that (i) directly modeling PRF using continuous function is very challenging and (ii) the dimension of PRF increases exponentially as a function of the pileup order. To overcome these significant obstacles, the methods described herein approximates the continuous PRF function using a small-scale pileup response matrix (PRM) estimated from calibration data 106. By this approximation, the forward model simplifies to a sequence of small matrices, which effectively coarse-grain the PRF at a manageable level of detail.

Figure 3:
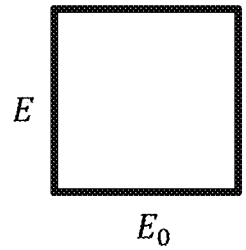
FIG. 3 shows the respective dimensions of pileup response matrices (PRMs) of a pileup response function (PRF), according to one implementation.
Figure 3:
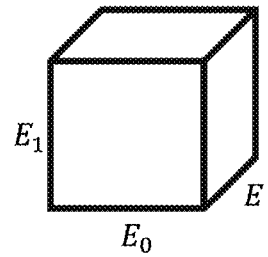
Figure 3:
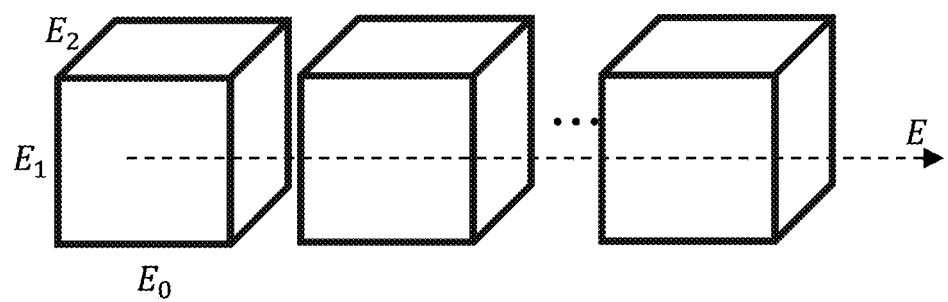

FIG. 3 illustrates the exponential growth of the PRF with respect to the pileup order, and the simplification provided by the methods described herein. Consider for example, the case in which PRM represent a continuous spectrum model for a 120 kVp X-ray source with a resolution of 1 kVp. FIG. 3A shows that the PRM for no-pileup would have 120×120 elements, corresponding to a two-dimensional matrix with indices for E and $E_0$ having a total of 14,400 elements. Similarly, the PRM representing first-order pileup includes 1,728,000 elements (i.e., 120×120×120 elements), and over 20 billion elements for the PRM representing second-order pileup (i.e., 120×120×120×120=20,7360,000 elements), illustrating that, due to exponential growth, even second-order pileup could present a data storage challenge.

However, in material decomposition procedure, only 2 unknowns (i.e., material components) are decomposed from the spectral component, suggesting that the energy can be resolved at a coarser resolution requiring fewer than 120 spectral components. Thus, recovering the continuous spectrum might not be necessary since the information provided by each of the 120 components is not unique (e.g., below the K-edge the attenuation is primarily due to only two processes—photoelectric absorption and Compton scattering—and all unique information can be conveyed in the absence of noise using only two spectral components). Therefore, to reduce the computation and storage costs, the continuous spectrum is coarse-grained by discretizing the spectra using only a few energy bins, dramatically reducing the size of the PRMs. It is noted that, even when the spectrum dimension uses only a few energy bins (i.e., more than two), the material decomposition is still an over-determined problem, including beneficial redundancy. The number of energy bins can be, e.g., 3, 4, 5, 6, 8, and 10, or other value as would be understood by a person of ordinary skill in the art.

Figure 4A:
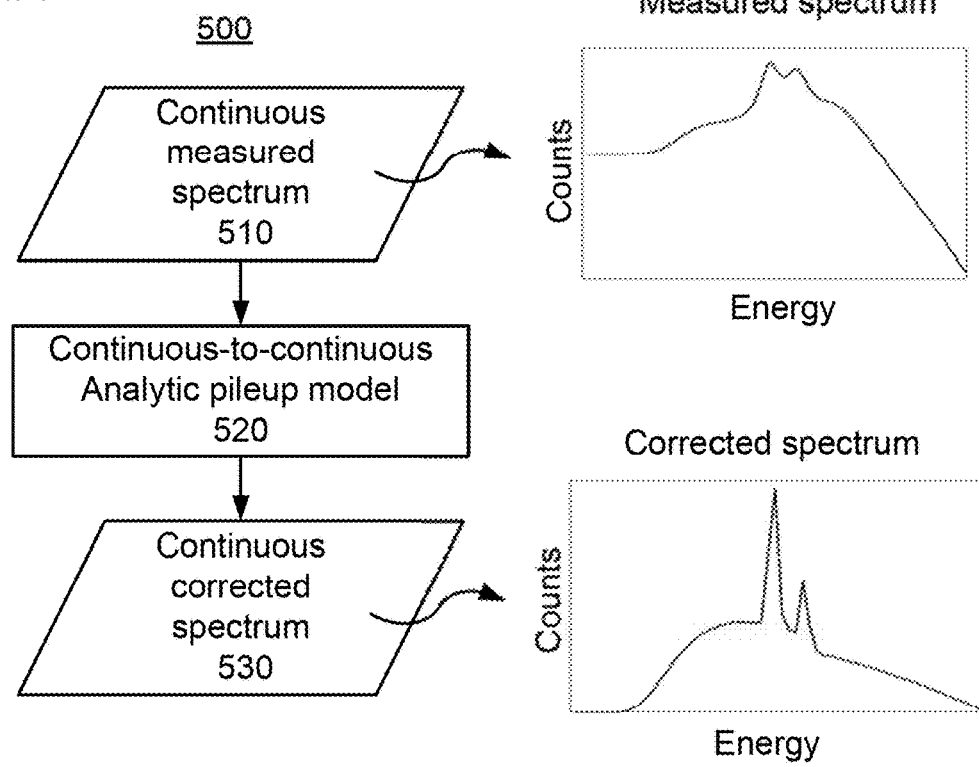
FIG. 4A shows an example of a method to correct measured X-ray spectrum using a continuous-to-continuous analytic pileup model, according to one implementation.
Figure 4B:
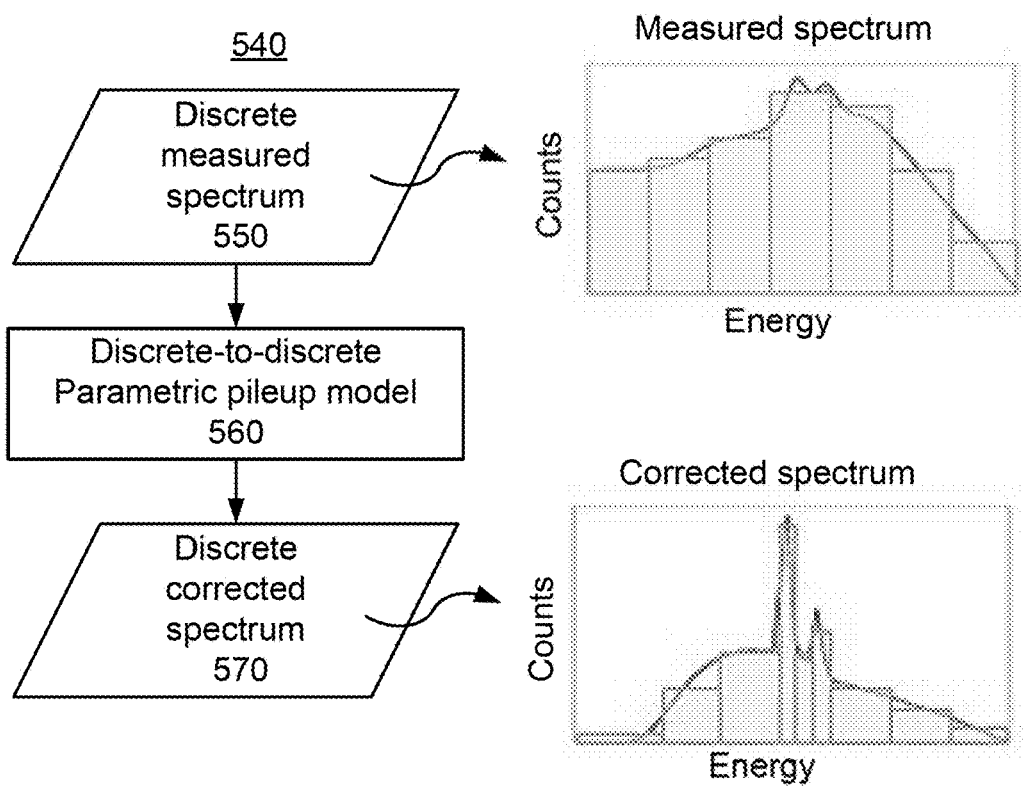
FIG. 4B shows an example of a method to correct measured X-ray spectrum using a discrete-to-discrete parametric pileup model, according to one implementation.

FIGS. 4A and 4B compare a continuous method 500 with a discrete (i.e., coarse-grained) method 540 of correcting pileup using respective pileup models. In FIG. 4A, a continuous-to-continuous analytic pileup model is applied at step 520 to map a continuous measured spectrum 510 (illustrated as the plot to the right of spectrum 510) to generate a continuous corrected spectrum 530 (illustrated as in the plot to the right of spectrum 530). As a comparison, FIG. 4B illustrates a discrete-to-discrete parametric pileup model being applied at step 560 to a discrete measured spectrum 550 (illustrated as the plot to the right of spectrum 540) to generate a discrete corrected spectrum 570 (illustrated as the plot to the right of spectrum 570). FIG. 4B shows a non-limiting example of the number of detected energy bins being seven and the number of corrected energy bins being nine. In certain implementations, the number of detected energy bins can equal the number of corrected energy bins. The span of the center energies of the discrete energy bins can be adjusted, e.g., based on empirical factors to optimize and improve image quality.

The simplification from a continuous-to-continuous analytic pileup model to a discrete-to-discrete parametric pileup model is described next. As discussed above, in the continuous domain the mth order pileup spectrum can be expressed by $$P(E|m,S_{in}) = \int \ldots \int dE_0 \ldots dE_m Pr(E|E_0, \ldots, E_m) S_{in}(E_0) \ldots S_{in}(E_m).$$

When the detected signals is translated into counts of the A energy bin $N_k$, the above expression simplifies to $$P(k|m) = \int \ldots \int dE_0 \ldots dE_m \int_{W_k}^{W_{k+1}} Pr(E|E_0, \ldots, E_m) S_{in}(E_0) \ldots S_{in}(E_m) dE$$

Next, basis functions can be introduced to represent the discretization of the energy bins corresponding to the various orders of pileup. These spectral basis functions can also be a square functions, defined as $$u_l(E) = \begin{cases} 1 & U_l < E < U_{l+1} \\ 0 & \text{otherwise} \end{cases},$$

and the count rate in $l^{th}$ energy bin is given by the expression $$X_l = \int dE_m u_l(E_m) S_{in}(E_m),$$

The energy spectrum $S_{in}(E_m)$ can then be approximated as $\Sigma_l u_l(E_m)$, which in turn allows the PRM to be approximated and further simplified as $$P(k|m) = \int_{W_k}^{W_{k+1}} dE \int \ldots \int dE_0 \ldots dE_m Pr(E|E_0, \ldots, E_m) \sum_l X_{l,0} u_l(E_0)$$

$$\ldots \sum_q X_{q,m} u_q(E_m) = \sum_l \ldots \sum_q X_l \times \ldots \times X_q$$

$$\int_{W_k}^{W_{k+1}} dE \int_{U_l}^{U_{l+1}} dE_0 \ldots \int_{U_q}^{U_{q+1}} dE_m Pr(E|E_0, \ldots, E_m) =$$

$$\sum_l \ldots \sum_q X_l \times \ldots \times X_q P_{k,l,\ldots,q}^{(m)}.$$

wherein, $P_{k,l,\ldots,q}^{(m)}$ are matrix elements of an m+2 dimensional matrix $P^{(m)} \in K_{out} \times K_{in}^{m+1}$, $K_{out}$ is the number of energy bins of the corrected spectrum, and $K_{in}$ is the number of energy bins of the measured/recorded spectrum. With the above approximation, the PRM for mth-order response has simplified to estimating the $K_{in}$ unknown parameters $X_l$ and calculating the matrix elements $P_{k,l,\ldots,q}^{(m)}$.

Consequently, the forward model formula can be expressed as $$y = \lambda_M \cdot \Delta T \cdot \sum_{m=0}^{\infty} \alpha_m P_m \overbrace{(x \otimes \ldots \otimes x)}^{m+1 \text{ terms}},$$

wherein $\overline{y}$ is a vector in which the kth element of the vector represents the measured mean count $N_k$ of the kth energy bin, $\alpha_m$ is a parameter representing the combination of coefficients of the mth-order pileup (e.g., $\alpha_m$ includes Pr(m), which is the probability for m X-rays being within the detection window as determined based on the Poisson statistics, and possibly other calibration factors), $P^{(m)}$ is the PRM defined above for pileup of order m, x is a vector of the true mean counts within respective energy bins (i.e., corrected for pileup). The symbol '⊗' is the tensor product (also known as the outer product or Kronecker product). To estimate the matrix elements of the PRMs, the forward model can be recast into $$y = \lambda_M \cdot \Delta T \cdot \sum_{m=0}^{\infty} \alpha_m X_m p_m = \lambda_M \cdot \Delta T \cdot \overline{X} p,$$

wherein the elements of $P_m$ have been reshaped from a matrix into the vector $p_m$, and $\overline{X}$ is a matrix generated using calibration data for $\alpha_m$ together with $X_m = I_{K_{out}} \otimes (x \otimes \ldots \otimes x)^T$. Whereas in the previous forward model formula the PRMs were treated as known and the vector x was treated as the argument, in this recast forward model formula, the vector x (i.e., $X_m$) is treated as known and the argument is the vector $p_m$ (i.e., the elements of $P_m$). Using this recast formulation, it is possible to estimate the PRMs, even without having an actual pulse-height analysis (PHA) associated with the ASIC. Given that the counts have a Poisson distribution, the PRMs can be estimated from the calibration data 106 by solving for the argument p that optimizes the maximum likelihood estimation (MLE):

$$\hat{p} = \underset{p \geq 0}{\operatorname{argmax}} \left\{ \sum_i \left\{ -\sum_{k=1}^{K_{out}} \overline{y}_{ik}(p) + \sum_{k=1}^{K_{out}} y_{ik} \log(\overline{y}_{ik}(p)) \right\} \right\},$$

wherein $\overline{y}_{ik}(p)$ is the mean count rate at energy bin measurement i, $y_{ik}$ is the measurement count rate with pileup effect (i.e., the measured/recorded counts in the projection data uncorrected for pileup). Using the above MLE, a unique solution is ensured for $\hat{p}$. The calibration data can include projection measurements in the absence of the object OBJ using various values to the current and voltage settings of the X-ray source of the X-ray imager (e.g., CT scanner).

Process 120 is now discussed in more detail. Having estimated the PRMs from the calibration data 106 as discussed above, the forward model is then ready to be used to determine a corrected spectrum (i.e., the mean counts before pileup x) from the recorded spectrum (i., the recorded/measured counts y). The corrected spectrum can be generated, for example, by optimizing an objective function (also referred to as a cost function). For example, the above objective function (i.e., the Poisson likelihood MLE) can be used, except the argument being optimized is the counts before pileup, x, rather than the elements of the PRMs. That is, the forward model formula can be expressed as $$y = \lambda_M \cdot \Delta T \cdot \sum_{m=0}^{\infty} \alpha_m P_m \overbrace{(x \otimes \ldots \otimes x)}^{m+1 \text{ terms}},$$

and the corrected spectrum can be generated by solving the optimization problem $$\hat{x} = \underset{x \geq 0}{\operatorname{argmax}} \left\{ \sum_i \left\{ -\sum_{k=1}^{K_{out}} \bar{y}_{ik}(p) + \sum_{k=1}^{K_{out}} y_{ik} \log(\bar{y}_{ik}(x)) \right\} \right\}.$$

Having solved for the corrected count x, material decomposition can then be performed using the corrected count x.

In certain implementations, the spectrum correction and the material decomposition can be integrated into a single step. For example, the corrected counts are given by $$x_i = \Delta T \int_{U_i}^{U_{i+1}} dE S_{in}(E),$$

and the incident spectrum is given by $$S_{in}(E) = S_{air}(E) \exp[-\mu_1(E) L_1 - \mu_2(E) L_2].$$

Thus, by approximating the attenuation coefficient of a given material component $n=\{1,2\}$ as $\mu_n(E) = \bar{\mu}_n^{(i)} + \Delta_n^{(i)}(E)$, wherein $\bar{\mu}_n^{(i)}$ is an average attenuation within the $i^{th}$ energy bin due to a predefined density of the $n^{th}$ material component, the corrected count $x_i$ can be expressed in terms of projection lengths $L=\{L_1, L_2\}$ of the material components, as given by the expression $$x_i = \Delta T \exp(-\bar{\mu}_1^{(i)} L_1) \exp(-\bar{\mu}_2^{(i)} L_2)$$
$$\int_{U_i}^{U_{i+1}} dE S_{air}(E) \exp[-\Delta \mu_1(E) L_1 - \Delta \mu_2(E) L_2],$$

which, prior to beam hardening corrections, can be approximated as $$x_i \approx \exp(-\bar{\mu}_1^{(i)} L_1) \exp(-\bar{\mu}_2^{(i)} L_2) x_i^{(air)},$$

wherein $x_i^{(air)} \int_{U_i}^{U_{i+1}} dE\, S_{air}(E)$. Accordingly, by substituting the above expression into the above optimization, the objective function can be recast to directly solve for the projection lengths $L=\{L_1, L_2\}$ such that the material decomposition is integrated with the pileup correction. For example the optimization problem can be formulated as $$\hat{L} = \underset{L \geq 0}{\operatorname{argmax}} \left\{ \sum_i \left\{ -\sum_{k=1}^{K_{out}} \bar{y}_{ik}(x(L)) + \sum_{k=1}^{K_{out}} y_{ik} \log(\bar{y}_{ik}(x(L))) \right\} \right\}$$
$$= \underset{L \geq 0}{\operatorname{argmax}} \left\{ \sum_i \left\{ -\sum_{k=1}^{K_{out}} \bar{y}_{ik}(L) + \sum_{k=1}^{K_{out}} y_{ik} \log(\bar{y}_{ik}(L)) \right\} \right\}.$$

So far, the objective functions mentioned have included only a data fidelity term subject to the constraint that the argument be positive. Additionally, the objective function can include additional constraints and regularization terms.

In general, any known method can be used to iteratively converge to the argument optimizing the objective function. For example, objective function can be optimized using an optimization search such as a steepest descent method, a gradient-based method, a genetic algorithm, a simulated annealing method, or other known method of searching for an argument that optimizes the objective function. Further, the argument used in the optimization search can be the spectrally resolved count rates or the projection lengths of material components.

To illustrate the use of different types of objective functions, the non-limiting example is used in which the projection lengths are the argument being used to optimize the objective function. That is, determining the optimal projection lengths $L=\{L_1, L_2\}$ by optimizing the objective function $\varphi(L_1, L_2)$ is illustrated. This objective function combines the measured projection data $y_m$ with corresponding calculated values $\bar{y}_m$ obtained from the detector model (i.e., forward model) discussed previously.

Several different objective functions $\varphi(L_1, L_2)$ are possible. In one implementation, the objective function is the least squares of the difference between the measured counts $y_m$ and the calculated counts from the forward model $\bar{y}_m$, i.e., $$\varphi(L_1, L_2) = \sum_m (y_m - \bar{y}_m)^2.$$

In one implementation, the objective function is the weighted least squares of the difference between the measured counts $y_m$ and the calculated counts $\bar{y}_m$, i.e., $$\varphi(L_1, L_2) = \sum_m \frac{(y_m - \bar{y}_m)^2}{\sigma_m^2},$$

where $\sigma_m$ is a measure of the measurement uncertainty of the $m^{th}$ energy bin of detector.

In one implementation, the objective function is the Poisson likelihood function, i.e., $$\varphi(L_1, L_2) = \sum_m [\bar{y}_m \log(y_m) - \bar{y}_m].$$

Process 120 can also include various other calibrations and corrections to the corrected counts and/or projection lengths, including beam hardening corrections, k-escape corrections, polar effect corrections, etc. as described in U.S. patent application Ser. No. 14/676,594 and U.S. patent application Ser. No. 14/593,818, which are both incorporated herein in their entirety.

Figure 5A:
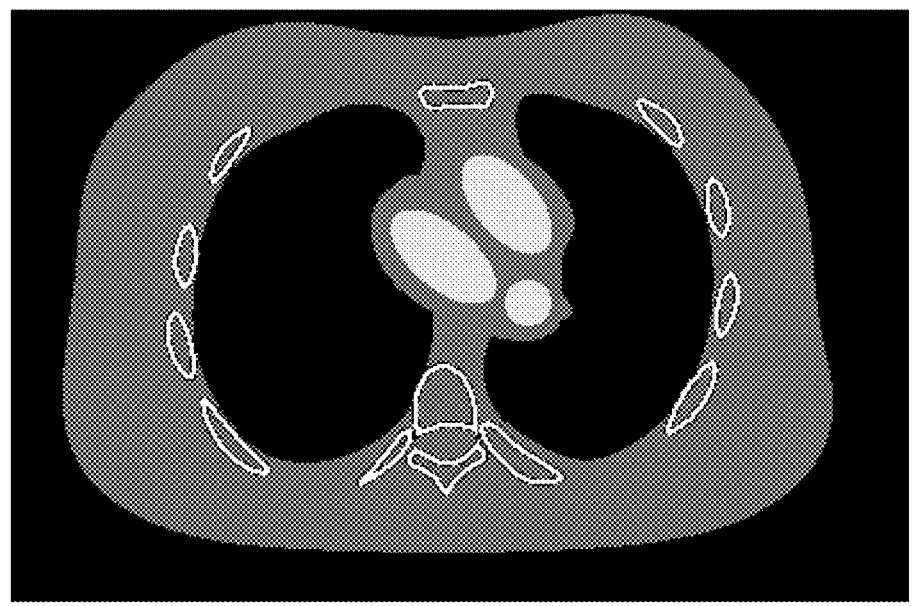
FIG. 5A shows an image of attenuation for a cross-section of a phantom.
Figure 5B:
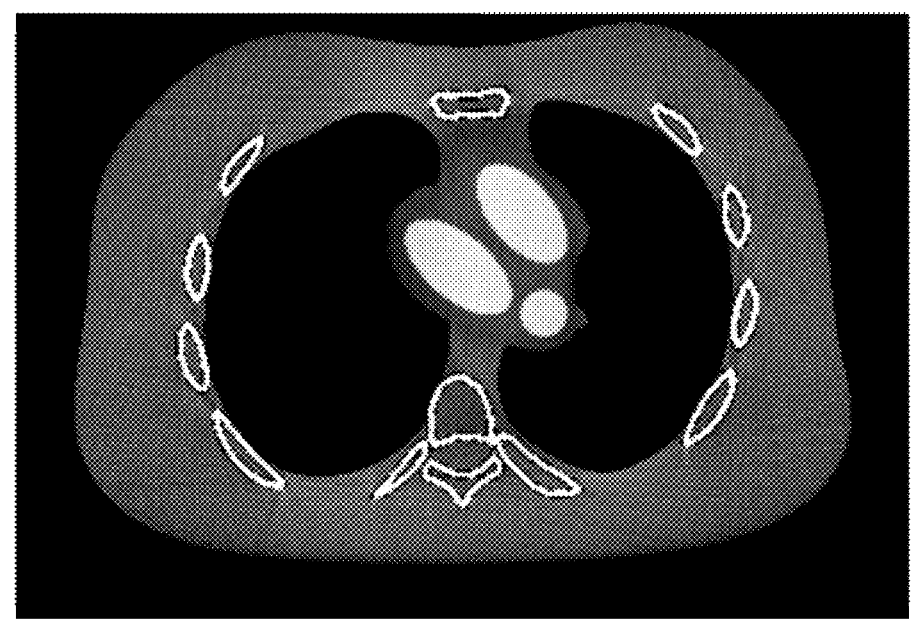
FIG. 5B shows a reconstructed image of the attenuation of the phantom that was reconstructed from projection data representing an ideal detector, according to one implementation.
Figure 5C:
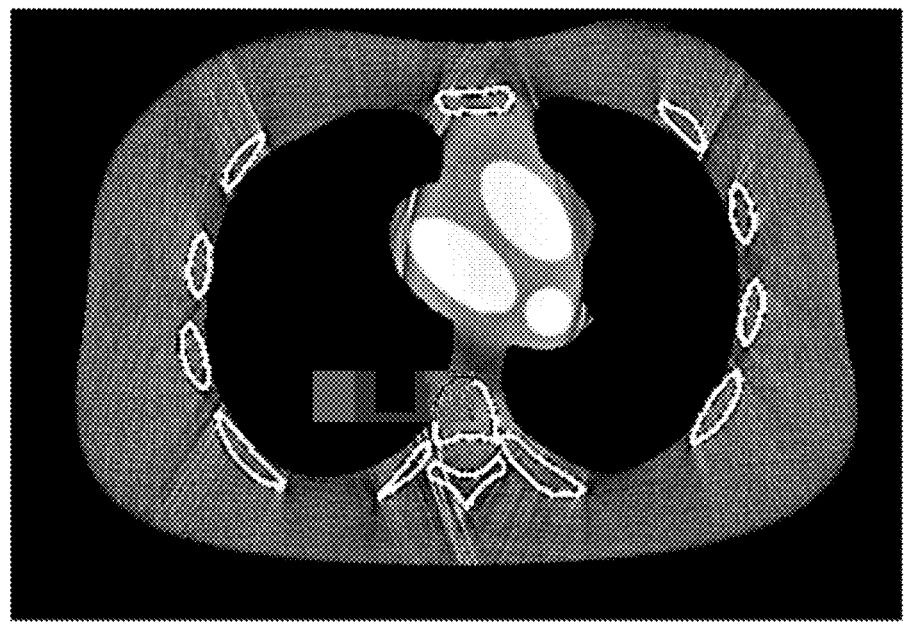
FIG. 5C shows a reconstructed image of the attenuation of the phantom that was reconstructed from a non-ideal detector that is corrected for the detector response but not for pileup, according to one implementation.
Figure 5D:
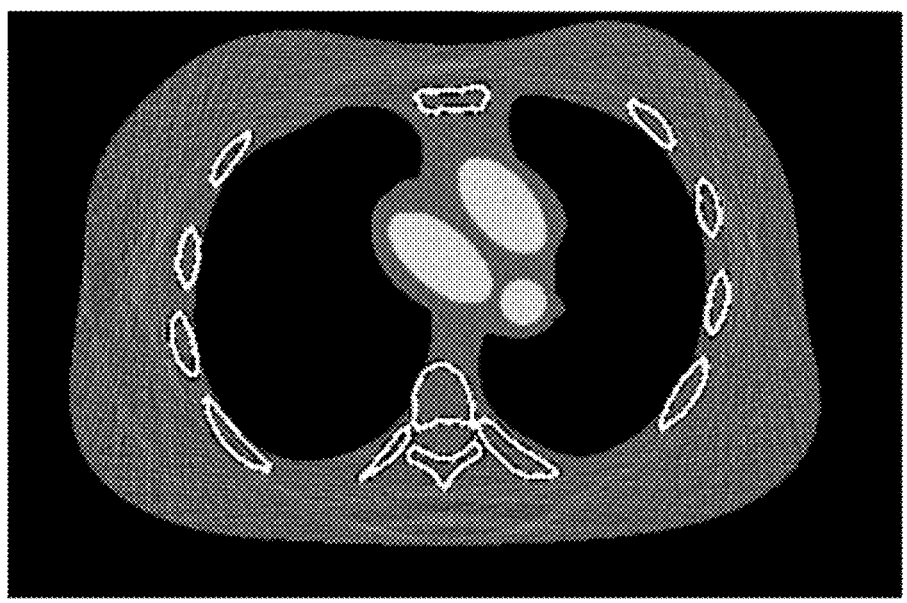
FIG. 5D shows a reconstructed image of the attenuation of the phantom that was reconstructed from a non-ideal detector that is corrected both for the detector response and for pileup, according to one implementation.

FIGS. 5A, 5B, 5C, and 5D show representative results for images reconstructed with and without using method 100. FIG. 5A shows a phantom used to simulate real and ideal detector responses. FIG. 5B shows a reconstructed image generated using an ideal detector unaffected by pileup, whereas FIGS. 5C and 5D show reconstructed images using a real detector response that includes pileup. In FIG. 5C, the projection data was not corrected for pileup but was corrected for the real detector response, the corrected projection data was then used to reconstruct the displayed attenuation image. In FIG. 5D, the projection data was corrected for both pileup and the real detector response, the corrected projection data was then used to reconstruct the displayed attenuation image. FIG. 5D illustrates that significant improvements to the image quality are realized by correcting for both pileup and the real detector response.

Figure 6A:
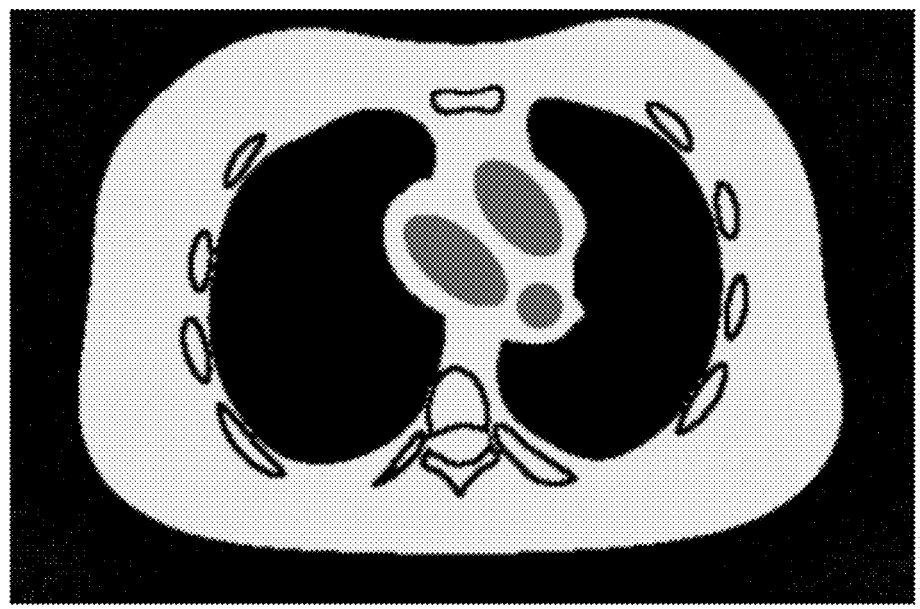
FIG. 6A shows an image of a water component of material decomposition of the attenuation of the phantom.
Figure 6B:
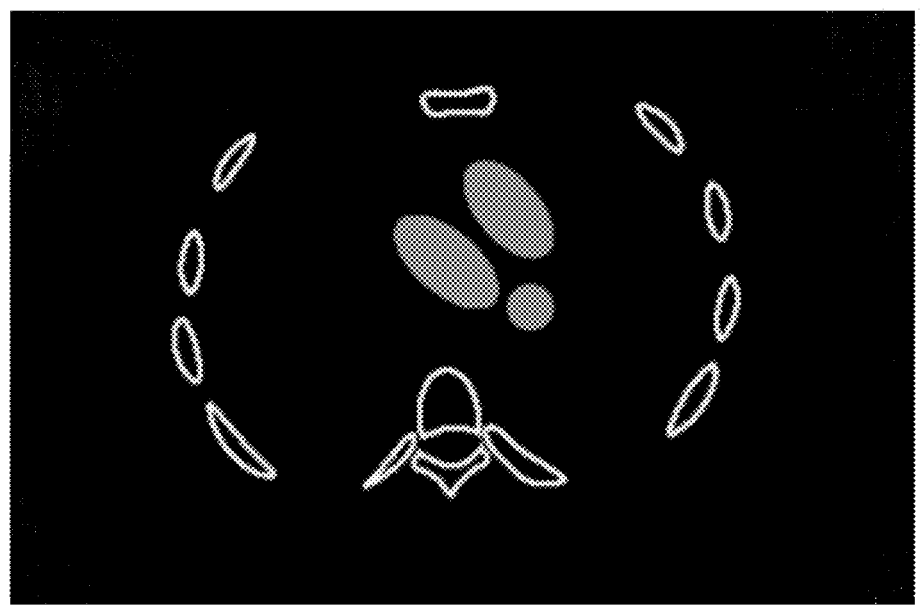
FIG. 6B shows an image of a bone component of the phantom.
Figure 7A:
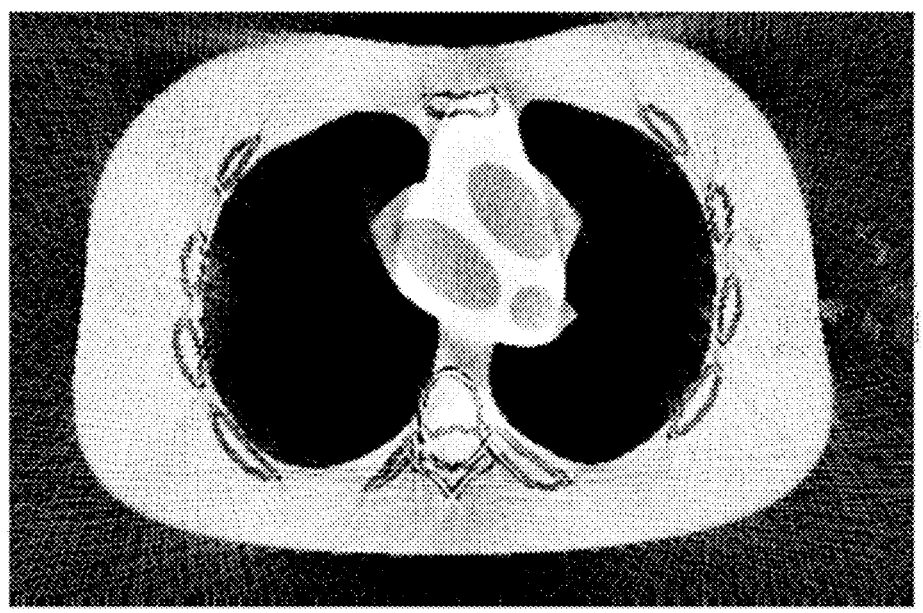
FIG. 7A shows an image of a water component reconstructed after material decomposition of the projection data corresponding to FIG. 5C, which is corrected for the detector response but not for pileup, according to one implementation.
Figure 7B:
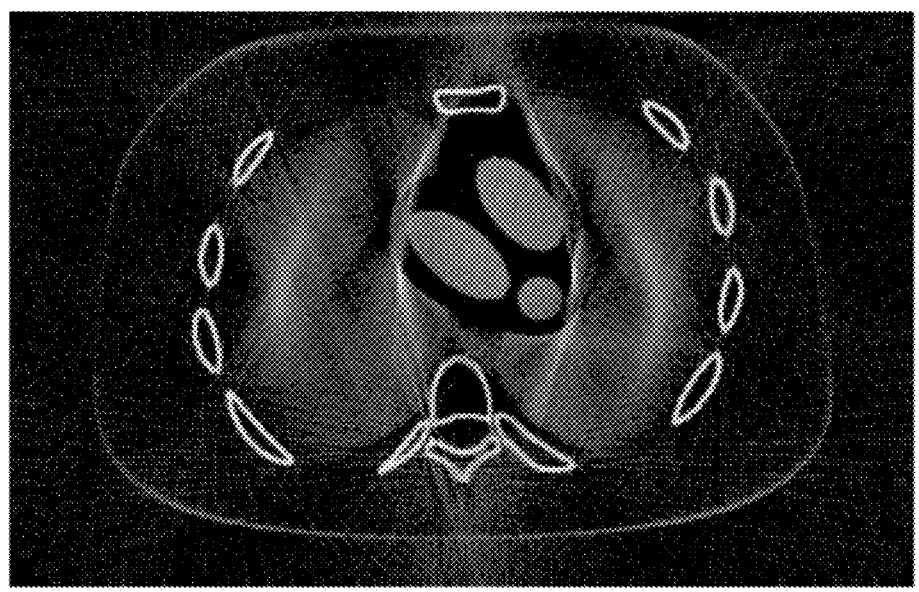
FIG. 7B shows an image of a bone component reconstructed after material decomposition of the projection data corresponding to FIG. 5C, according to one implementation.
Figure 8A:
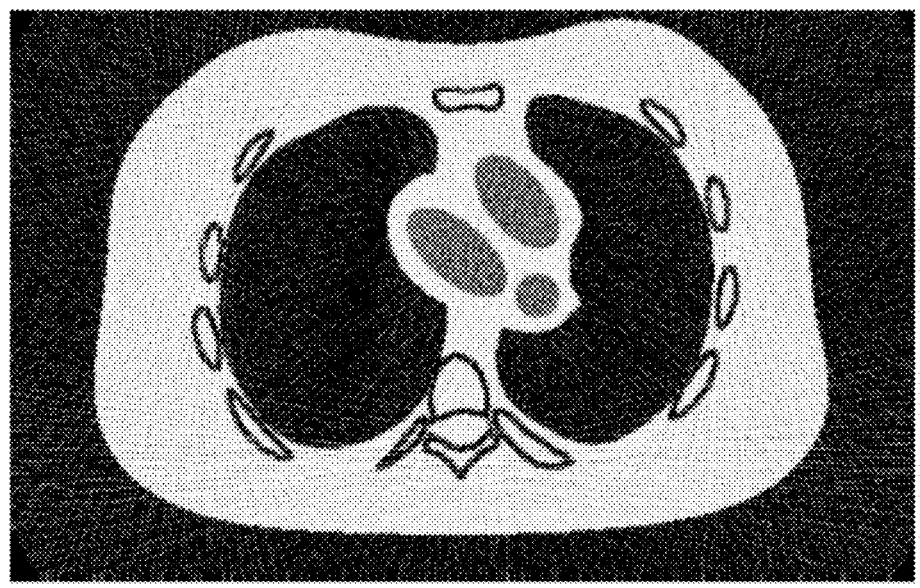
FIG. 8A shows an image of a water component reconstructed after material decomposition of the projection data corresponding to FIG. 5D, which is corrected both for the detector response and for pileup, according to one implementation.
Figure 8B:
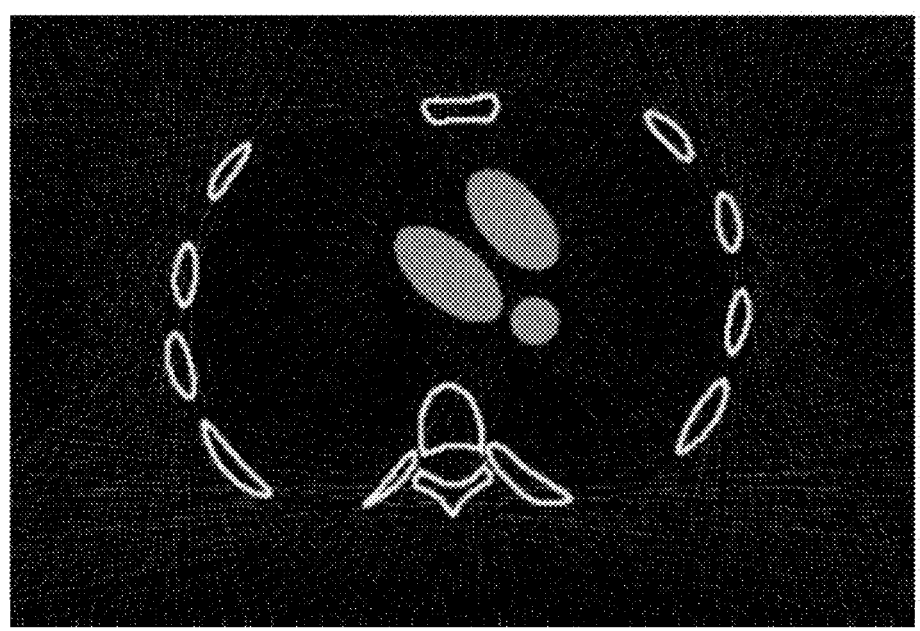
FIG. 8B shows an image of a bone component reconstructed after material decomposition of the projection data corresponding to FIG. 5D, according to one implementation.

Similarly. FIGS. 6A and 6B show the phantom from FIG. 5A decomposed into material components corresponding to water and bone, respectively. FIGS. 7A and 7B show a material decomposition into water and bone, respectively, using projection data that was not corrected for pileup but was corrected for the real detector response. FIGS. 8A and 8B show a material decomposition into water and bone, respectively, using projection data that was corrected for both pileup and the real detector response. Comparing FIGS. 8A and 8B with their counterparts in FIGS. 7A and 7B, the improvements provided by the pileup corrections described herein are once again clearly evident.

Figure 9:
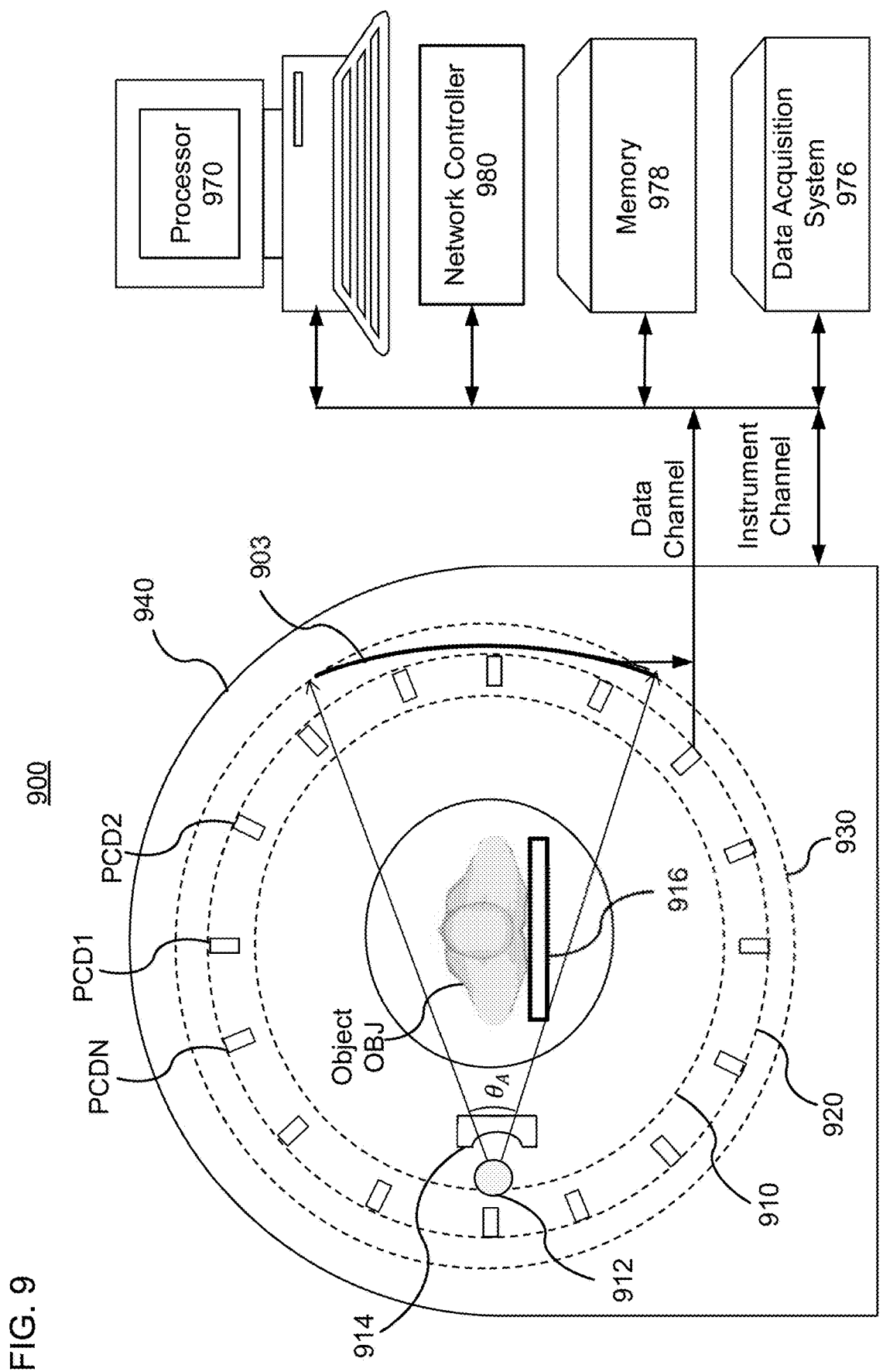
FIG. 9 shows a schematic of an implementation of a computed tomography (CT) scanner, according to one implementation.

FIG. 9 shows a computed tomography (CT) scanner 900 having both energy-integrating detectors arranged in a third-generation geometry and PCDs arranged in a fourth-generation geometry. Illustrated in FIG. 9 is an implementation for placing the PCDs in a predetermined fourth-generation geometry in combination with a detector unit 903 in a predetermined third-generation geometry in a CT scanner system. The diagram illustrates relative positions among the X-ray source 912, the collimator/filter 914, the X-ray detector 903, and the photon-counting detectors PCD1 through PCDN. The projection data 104 can be obtained using the CT scanner 900, and the projection data 104 can be obtained using the CT scanner 900 in which the detector unit 903 is omitted.

In addition to the configuration of the X-ray source 912 and the detectors including the detector unit 903 and the PCDS show in FIG. 9, other types and combinations of X-ray detectors and X-ray source can be used to obtain the projection data. For example, either the detector unit 903 or the PCDS could be omitted from the scanner shown in FIG. 9 and the scanner could still obtain projection data, albeit different from the projection data obtained using the complete system shown in FIG. 9. Further, kV switching could be used with energy-integrating detectors or PCDs. In certain implementations, the PCDS can be direct X-ray detectors using semiconductors to convert the X-rays directly to photoelectrons without first generating scintillation photons. Additionally, in certain implementations, a broadband X-ray source can be used with spectrally-resolving X-ray detectors. These spectrally-resolving X-ray detectors can include PCDs in any configurations (e.g., a predetermined third-generation geometry or a predetermined fourth-generation geometry) or energy-integrating detectors preceded by respective spectral filters. In certain implementations, the X-ray source can include multiple narrow-band X-ray sources, such as in a dual source CT scanner. In general, any known combination of detector type and configuration together with any known type or combination of X-ray sources can be used to generate the projection data.

Returning to FIG. 9, FIG. 9 also shows circuitry and hardware for acquiring, storing, processing, and distributing X-ray projection data. The circuitry and hardware include: a processor 970, a network controller 980, a memory 978, and a data acquisition system 976.

In one alternative implementation, the CT scanner includes PCDs but does not include the energy-integrating detector unit 903.

As the X-ray source 912 and the detector unit 903 are housed in a gantry 940 and rotate around circular paths 910 and 930 respectively, the photon-counting detectors PCDs and the detector unit 903 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 903 continuously detect the X-ray radiation that has been transmitted and output the detected signals as the detector unit 903 rotates. In one implementation, the detector unit 903 has densely placed energy-integrating detectors in predetermined channel and segment directions on the detector unit surface.

In one implementation, the X-ray source 912, the PCDs and the detector unit 903 collectively form three predetermined circular paths that differ in radius. At least one X-ray source 912 rotates along a first circular path 910 while the photon-counting detectors are sparsely placed along a second circular path 920. Further, the detector unit 903 travels along a third circular path 930. The first circular path 910, second circular path 920, and third circular path 930 can be determined by annular rings that are rotatably mounted to the gantry 940.

Additionally, alternative embodiments can be used for placing the photon-counting detectors in a predetermined fourth-generation geometry in combination with the detector unit in a predetermined third-generation geometry in the CT scanner.

In one implementation, the X-ray source 912 is optionally a single energy source. In another implementation, the X-ray source 912 is configured to perform a k-switching function for emitting X-ray radiation at a predetermined high-level energy and at a predetermined low-level energy. In still another alternative embodiment, the X-ray source 912 is a single source emitting a broad spectrum of X-ray energies. In still another embodiment, the X-ray source 912 includes multiple X-ray emitters with each emitter being spatially and spectrally distinct.

The detector unit 903 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 903 to a data acquisition system 976, a processor 970, memory 978, network controller 980. The data acquisition system 976 controls the acquisition, digitization, and routing of projection data from the detectors. The data acquisition system 976 also includes radiography control circuitry to control the rotation of the annular rotating frames 910 and 930. In one implementation data acquisition system 976 will also control the movement of the bed 916, the operation of the X-ray source 912, and the operation of the X-ray detectors 903. The data acquisition system 976 can be a centralized system or alternatively it can be a distributed system. In an implementation, the data acquisition system 976 is integrated with the processor 970. The processor 970 performs functions including reconstructing images from the projection data, pre-reconstruction processing of the projection data, and post-reconstruction processing of the image data. The processor 970 also performs the functions and methods described herein.

The pre-reconstruction processing of the projection data can include correcting for detector calibrations, detector nonlinearities, polar effects, noise balancing, and material decomposition. Additionally, the pre-reconstruction processing can include preforming various steps of method 100, including processes 110 and 120.

Post-reconstruction processing can include filtering and smoothing the image, volume rendering processing, and image difference processing as needed. For example, the post-reconstruction processing can be performed using various steps of method 100 (e.g., process 140)

The image-reconstruction process can be performed using filtered back-projection, iterative-image-reconstruction methods, or stochastic-image-reconstruction methods.

Additionally, the image-reconstruction processing can include a combined process of reconstructing and denoising the reconstructed images using various steps of method 100 (e.g., process 130).

Both the processor 970 and the data acquisition system 976 can make use of the memory 976 to store, e.g., the projection data 104, reconstructed images, the calibration data 106, various other parameters, and computer programs.

The processor 970 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 978 can be a hard disk drive, CD-ROM drive, DVD drive, FLASH drive, RAM, ROM or any other electronic storage known in the art.

The network controller 980, such as an Intel Ethernet PRO network interface card from Intel Corporation of America, can interface between the various parts of the CT scanner. Additionally, the network controller 980 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A computed tomography (CT) scanner, comprising:
a gantry including a rotating member configured to rotate about an opening configured to accommodate an object being imaged,
an X-ray source fixed to the rotating member and configured to radiate X-rays towards the opening of the gantry;
an X-ray detector comprising a plurality of photon-counting detector elements, the X-ray detector configured to detect the X-rays transmitted from the X-ray source after having been transmitted through the opening in the gantry, which is configured to accommodate an object being imaged, the X-ray detector generating projection data comprising recorded counts detected at respective photon-counting detector elements comprising the X-ray detector, and the recorded counts (i) correspond to energy bins of the X-ray detector, (ii) are affected by pileup of X-rays within a detection time window, and (iii) have a pileup-affected spectrum that is distorted relative to a true spectrum of the detected X-rays; and
processing circuitry configured to
obtain a forward model of pulse pileup that estimates the pileup-affected spectrum of the recorded counts based on an input of a pileup-corrected spectrum proposed to represent the true spectrum of the detected X-rays, the forward model including parameters specific to the respective photon-counting detector elements, and the forward model representing two or more orders of pulse pileup and including a respective pileup response matrix for each one of the two or more orders of pulse pileup, and
correct the projection data using the forward model to generate corrected projection data, wherein
an nth-order of pulse pileup of the two or more orders of pulse pileup represents n+1 X-rays being detected at one of the photon-counting detector elements within a detection time window, and n is a positive integer.

2. The CT scanner according to claim 1, wherein the processing circuitry is further configured to correct the projection data by
optimizing a value of an objective function to determine an optimal value of an argument of the objective function, the objective function representing agreement between the pileup-affected spectrum of the obtained projection data and the estimated pileup-affected spectrum generated using the forward model.

3. The CT scanner according to claim 2, wherein the processing circuitry is further configured to obtain the forward model, wherein
the argument of the objective function, which is being used to optimize the objective function, is one of the input of the pileup-corrected spectrum in the forward model and projection lengths of a material decomposition, which are used to determine the input of the pileup-corrected spectrum in the forward model, wherein, when the argument is the projection lengths, the correcting of the projection data using the forward model to generate the corrected projection data is performed such that the corrected projection data includes the projection lengths, and the processing circuitry is further configured to reconstruct material-component images using the projection lengths of the corrected projection data, and, when the argument is the spectrum of X-rays detected at the one of the photon-counting detector elements, the correcting of the projection data using the forward model to generate the corrected projection data is performed such that the corrected projection data includes corrected counts corresponding to other energy bins, and the processing circuitry is further configured to decompose the corrected counts into projection lengths of the material decomposition and reconstruct material-component images using the projection lengths.

4. The CT scanner according to claim 2, wherein the processing circuitry is further configured to correct the projection data using the objective function that is one of a Poisson likelihood function, a least-squares difference function, and a weighted least-squares difference function.

5. The CT scanner according to claim 1, wherein the processing circuitry is further configured to obtain the forward model, wherein, in the forward model, the input spectrum of the detected X-rays is determined using a multiplication between an attenuation coefficient of a material component and a projection length for the material component, for each material component of a material decomposition.

6. The CT scanner according to claim 1, wherein the processing circuitry is further configured to obtain the forward model, wherein, in forward model, the spectrum of the recorded counts is partitioned according to the energy bins of the X-ray detector, and the input spectrum representing the detected X-rays is partitioned according to other energy bins having one or more different partitions than the energy bins of the X-ray detector.

7. The CT scanner according to claim 1, wherein the processing circuitry is further configured to obtain the forward model, wherein, in the forward model for each one of the photon-counting detector elements, each nth-order of pulse pileup of the two or more orders of pulse pileup is scaled by a Poisson-distributed probability of n+1 X-rays being detected at the one of the photon-counting detector elements within the detection time window.

8. The CT scanner according to claim 1, wherein the processing circuitry is further configured to decompose the corrected projection data into material components to generate a material decomposition, and reconstruct material-component images of the object being imaged using the material decomposition.

9. The CT scanner according to claim 1, wherein the processing circuitry is further configured to correct the projection data using the forward model to generate the corrected projection data, wherein the correcting of the projection data using the forward model integrates a material decomposition with correcting the pileup-affected spectrum of the recorded counts of the obtained projection data to generate the corrected projection data, which includes projection lengths of the material decomposition, and the processing circuitry is further configured to reconstruct material-component images of the object being imaged using the corrected projection data.

10. The CT scanner according to claim 1, wherein the processing circuitry is further configured to generate the forward model using calibration data representing projection data generated by the X-ray detector in an absence of the object being imaged, the parameters specific to the respective photon-counting detector elements being determined as an argument that optimizes an objective function that represents agreement between the pileup-affected spectrum of the obtained projection data and the estimated pileup-affected spectrum generated using the forward model, the argument of the objective function being the parameters specific to the respective photon-counting detector elements, store, in a non-transitory computer readable medium, the parameters specific to the respective photon-counting detector elements that optimize the objective function, and perform the obtaining of the forward model by reading, from the non-transitory computer readable medium, the stored parameters specific to the respective photon-counting detector elements.

11. The CT scanner according to claim 1, wherein the processing circuitry is further configured to obtain the forward model, wherein, in forward model, a number of the energy bins of the X-ray detector is equal to a number of the other energy bins, which is less than seven.

12. The CT scanner according to claim 1, wherein the processing circuitry is further configured to obtain the projection data, wherein the photon-counting detector elements are semiconductor detectors comprising one or more of cadmium telluride (CdTe), cadmium zinc telluride (CZT), silicon (Si), mercuric iodide (HgI2), and gallium arsenide (GaAs).

* * * * *